US012806375B2

(12) United States Patent
Zhou et al.

(10) Patent No.: US 12,806,375 B2
(45) Date of Patent: Nov. 24, 2026

(54) TRANSLUMINAL INTERVENTION SYSTEM

(71) Applicant: CTC Medical Technology (Beijing) Co., LTD, Beijing (CN)

(72) Inventors: Haiyan Zhou, Beijing (CN); Meng Shao, Beijing (CN); Lei Zhao, Beijing (CN); Haiyun Huang, Beijing (CN)

(73) Assignee: CTC Medical Technology (Beijing) Co., LTD, Beijing (CN)

( * ) Notice: Subject to any disclaimer, the term of this patent is extended or adjusted under 35 U.S.C. 154(b) by 281 days.

(21) Appl. No.: 18/710,481

(22) PCT Filed: Nov. 15, 2022

(86) PCT No.: PCT/CN2022/132067
§ 371 (c)(1),
(2) Date: May 15, 2024

(87) PCT Pub. No.: WO2023/093579
PCT Pub. Date: Jun. 1, 2023

(65) Prior Publication Data

US 2026/0166272 A1 Jun. 18, 2026

(30) Foreign Application Priority Data

Nov. 23, 2021 (CN) ......................... 202111393803.4

(51) Int. Cl.
*A61M 25/01* (2006.01)
*A61M 25/09* (2006.01)

(52) U.S. Cl.
CPC .. *A61M 25/0113* (2013.01); *A61M 25/09041* (2013.01)

(58) Field of Classification Search
CPC ........ A61M 25/0113; A61M 25/09041; A61M 25/01; A61M 25/09; A61M 25/0172; A61M 25/0169; A61M 25/0116
See application file for complete search history.

(56) References Cited

U.S. PATENT DOCUMENTS

2017/0056616 A1 3/2017 Leeflang et al.
2017/0105804 A1 4/2017 Yu
2021/0236217 A1 8/2021 Sharon et al.

FOREIGN PATENT DOCUMENTS

CN 110680975 A 1/2020
CN 110913940 A 3/2020
(Continued)

OTHER PUBLICATIONS

Feb. 2, 2024—(CN) Office Action—App 202111393803.4—Eng Trans.

(Continued)

*Primary Examiner* — Tasnim Mehjabin Ahmed
(74) *Attorney, Agent, or Firm* — Banner & Witcoff, Ltd.

(57) ABSTRACT

A transluminal intervention system, comprises medical catheter and guidewires and a medical catheter or guidewire driver for driving the medical catheter or guidewires. The medical catheter or guidewire driver comprises: a base; and a regulation and control mechanism, fixedly mounted on the base and comprising a first regulation and control assembly and a second regulation and control assembly arranged at intervals for driving the medical catheter or guidewire to rotate and move, the base and the regulation and control mechanism are combined, and the regulation and control mechanism and the medical catheter or guidewire are integrated on the base, thereby achieving structural compactness and high integration level. The regulation and control mechanism with a fixed position drives the medical catheter or guidewire to rotate and move, such that there is no need to adaptively regulate a proximal end of the medical catheter or guidewire according to a distal end of the medical catheter or guidewire, and the medical catheter or guidewire is enabled to run in a spiral manner under superposition of rotation and movement acting forces, accurately reproducing the actions of the medical personnel. The transluminal (Continued)

intervention system has a simple structure, a compact arrangement and a high integration level, is easy to operate, and achieves a high catheter and guidewire delivery efficiency.

16 Claims, 4 Drawing Sheets

(56) References Cited

FOREIGN PATENT DOCUMENTS

| | | | |
|---|---|---|---|
| CN | 111110989 | A | 5/2020 |
| CN | 112120745 | A | 12/2020 |
| CN | 212662442 | U | 3/2021 |
| CN | 112891707 | A | 6/2021 |
| CN | 113082463 | A | 7/2021 |
| CN | 213609264 | U | 7/2021 |
| CN | 113509302 | A | 10/2021 |
| CN | 113598947 | A | 11/2021 |
| CN | 113633383 | A | 11/2021 |
| CN | 114177482 | A | 3/2022 |
| CN | 114177487 | A | 3/2022 |
| IT | 201800009380 | A1 | 4/2020 |

OTHER PUBLICATIONS

May 29, 2023—(CN) Office Action—App 202111393803.4—Eng Trans.
Feb. 14, 2023—(PCT/CN) Search Report—App 2022132067—Eng Trans.
Feb. 4, 2025—(EP) Supplementary Search Report—App 22897662.7.

TRANSLUMINAL INTERVENTION SYSTEM

CROSS-REFERENCE TO RELATED APPLICATIONS

The present application is a U.S. National Phase filing of International Application No. PCT/CN2022/132067, filed on Nov. 15, 2022, and claiming the priority of Chinese Patent Application No. 202111393803.4 entitled "Transluminal Intervention System" and filed with China National Intellectual Property Administration on Nov. 23, 2021, the content of which is incorporated herein by reference in its entirety.

FIELD OF THE INVENTION

The present application belongs to the technical field of interventional treatment, and specifically relates to a transluminal intervention system.

BACKGROUND OF THE INVENTION

Organ lesions may be treated by using various treatment means, such as surgical removal of lesion tissues or interventional treatment, wherein, the interventional treatment is a minimally invasive therapy that uses a modern high-tech means. That is, under the guidance of a medical imaging device, a specially-made precision instrument such as a catheter, a guide wire, etc. is introduced into a human body by using a catheter delivery system, to diagnose and locally treat morbidness in the human body. Compared to the surgical therapy, the interventional treatment is less invasive.

For example, in an interventional surgery for liver, a guide catheter is inserted into the femoral artery of a patient and located near an arterial orifice of the patient's liver by using a catheter delivery system. Usually, a guide wire is inserted into the guide catheter via a hemostatic valve and is manipulated through the patient's arterial system until the guide wire reaches the lesion site. Then, a percutaneous device is moved along the guide wire until it reaches tissues to be intervened. At this time, the guide wire is drawn out, and chemotherapy drugs or embolic agents are injected into blood vessels through a micro-catheter to block the blood vessels to reduce blood supply of tumor, thereby achieving an objective of inhibiting tumor growth.

A catheter or guidewire for the interventional treatment typically has a fixed length, with a catheter or guidewire proximal end serving as a fixing end and a catheter or guidewire distal end serving as a moving end. During the movement of the catheter or guidewire distal end, in order to prevent the catheter or guidewire from being broken or damaged due to pulling, position of the catheter or guidewire proximal end, which serves as the fixing end, needs to be regulated to cooperate with the movement of the catheter or guidewire distal end, resulting in that the operations during the catheter or guidewire delivery process are cumbersome and it is difficult for structural integration.

SUMMARY OF THE INVENTION

Technical Solution

In view of the above defects or deficiencies in the prior art, the present application provides a transluminal intervention system, which has a simple structure, a compact arrangement and a high integration level, is easy to operate, and achieves a high catheter or guidewire delivery efficiency.

To achieve the above objectives, according to one aspect of the present application, there is provided a transluminal intervention system, which comprises multiple medical catheters or guidewires and a medical catheter or guidewire driver for driving the multiple medical catheters or guidewires, wherein, the medical catheter or guidewire driver comprises:

a base; and a regulation and control mechanism, fixedly mounted on the base and comprising a first regulation and control assembly and a second regulation and control assembly arranged at intervals for driving the medical catheters or guidewires to rotate and move, wherein, the first regulation and control assembly comprises a first driving seat and a second driving seat for driving movement of the medical catheter or guidewire, and a first catheter or guidewire fixture for fixing the medical catheter or guidewire and driving rotation of the medical catheter or guidewire; and the second regulation and control assembly comprises a second catheter or guidewire fixture for fixing the medical catheter or guidewire and driving rotation of the medical catheter or guidewire, and a third driving seat for driving movement of the medical catheter or guidewire; and within the first regulation and control assembly and the second regulation and control assembly, the medical catheters or guidewires are configured to be curved.

In some embodiments, the base comprises a base plate, and the regulation and control mechanism is inserted and fixed on the base plate, such that all of the multiple medical catheters or guidewires are arranged on a same side of the base plate at intervals.

In some embodiments, the first catheter or guidewire fixture, the second driving seat, the first driving seat, the third driving seat, and the second catheter or guidewire fixture are sequentially arranged along a length direction of the base plate at intervals.

In some embodiments, the base plate is provided with multiple guide structures for regulating deflection of the medical catheters or guidewires, and the multiple guide structures are arranged along the length direction of the base plate at intervals.

In some embodiments, the guide structures comprise a first guide structure for regulating the medical catheter or guidewire between the first catheter or guidewire fixture and the second driving seat, a second guide structure for regulating the medical catheter or guidewire between the second driving seat and the first driving seat, and a third guide structure for regulating the medical catheter or guidewire between the third driving seat and the second catheter or guidewire fixture.

In some embodiments, the first guide structure, the second guide structure, and the third guide structure are same in structure and each comprises:

a bottom plate, fixedly mounted on the base plate; and two limit plates, configured to limit a movement range of the medical catheter or guidewire and arranged on the bottom plate at intervals.

In some embodiments, a cover plate is provided between the two limit plates, and a limiting accommodation space is formed between the cover plate and the bottom plate.

In some embodiments, the first catheter or guidewire fixture and the second catheter or guidewire fixture are same in structure and each comprises a fixing seat bracket protruding from the base plate and a catheter or guidewire clamp rotatably mounted on the fixing seat bracket.

In some embodiments, the base plate is provided with a catheter or guidewire clamp driving unit for driving rotation of the catheter or guidewire clamp, and the catheter or guidewire clamp driving unit comprises:

a rotation driving motor, embedded on the base plate; and a catheter or guidewire clamp transmission component, connected between the rotation driving motor and the catheter or guidewire clamp in a transmission manner.

In some embodiments, the catheter or guidewire clamp transmission component is a bevel gear transmission component and comprises a main drive gear protruding from the rotation driving motor and a driven gear protruding from the catheter or guidewire clamp which are meshed with each other.

In some embodiments, the first driving seat, the second driving seat, and the third driving seat are same in structure and each comprises a wheel driving motor mounted on the base plate, and a catheter or guidewire driving wheel and a catheter or guidewire idler wheel protruding from the base plate, wherein the medical catheter or guidewire is clamped between the catheter or guidewire driving wheel and the catheter or guidewire idler wheel.

In some embodiments, both of an axis of the catheter or guidewire driving wheel and an axis of the catheter or guidewire idler wheel are perpendicular to the base plate; and/or, the wheel driving motor and the medical catheter or guidewire are arranged on two sides of the base plate, respectively.

In some embodiments, a driving direction of the first driving seat is opposite to a driving direction of the second driving seat; and/or, a driving direction of the third driving seat is the same as the driving direction of the first driving seat.

In some embodiments, the medical catheter or guidewire driver comprises a fixing seat and the base that is slidably mounted on the fixing seat and able to slide along a length direction of the fixing seat.

In some embodiments, the regulation and control mechanism further comprises a third regulation and control assembly for driving rotation and movement of the medical catheter or guidewire, wherein the third regulation and control assembly comprises:

a fourth driving seat, configured to drive movement of the medical catheter or guidewire and fixedly mounted on the fixing seat; and a rotation driving seat, fixedly mounted on the base plate and configured to fix the medical catheter or guidewire and drive rotation of the medical catheter or guidewire.

In some embodiments, the fixing seat comprises an L-shaped plate, which comprises a first directional plate portion and a second directional plate portion that are sequentially connected, the base plate is provided with a sliding component on a surface thereof, and the first directional plate portion is provided with a sliding rail for sliding the sliding component on a surface thereof.

Advantageous Effects

In the transluminal intervention system of the present application, the base and the regulation and control mechanism are combined, and the regulation and control mechanism and the medical catheters or guidewires are integrated on the base, thereby achieving structural compactness and high integration level. The regulation and control mechanism with a fixed position drives the medical catheters or guidewires to rotate and move, such that, there is no need to adaptively regulate a proximal end of the medical catheter or guidewire according to a distal end of the medical catheter or guidewire, and furthermore, the medical catheter or guidewire is enabled to run in a spiral manner under superposition of rotation and movement acting forces, so as to accurately reproduce the actions of the medical personnel. The transluminal intervention system has a simple structure, a compact arrangement and a high integration level, is easy to operate, and achieves a high catheter or guidewire delivery efficiency.

BRIEF DESCRIPTION OF THE DRAWINGS

The accompanying drawings are configured to provide an understanding of the present application and form a part of the specification. They are configured together with the specific embodiments below to explain the present application, but do not constitute a limitation to the present application, in which.

DESCRIPTION OF REFERENCE NUMERALS

Figure 1:
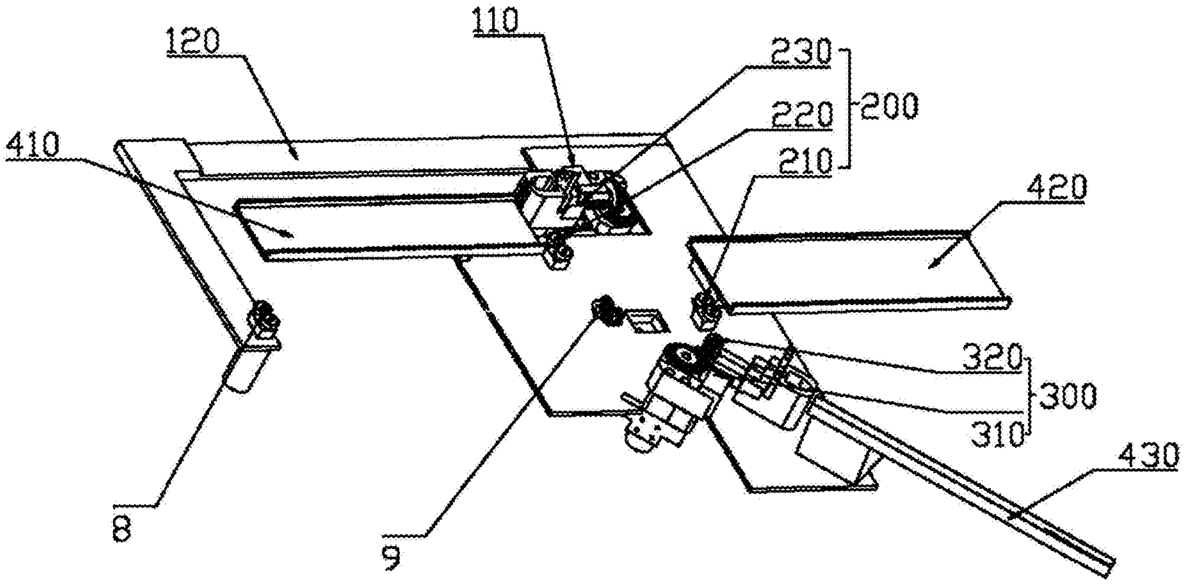
FIG. 1 is a schematic view of a stereostructure of a transluminal intervention system according to a specific embodiment of the present application.

| | | | |
|---|---|---|---|
| 110 | Base | 120 | Fixing seat |
| 200 | First regulation and control assembly | | |
| 210 | First driving seat | 220 | Second driving seat |
| 230 | First catheter or guidewire fixture | | |
| 300 | Second regulation and control assembly | | |
| 310 | Second catheter or guidewire fixture | 320 | Third driving seat |
| 400 | Guide structure | | |
| 410 | First guide structure | 420 | Second guide structure |
| 430 | Third guide structure | | |
| 41 | Bottom plate | 42 | Limit plates |
| 43 | Cover plate | | |
| 1 | Fixing seat bracket | 2 | Catheter or guidewire clamp |
| 3 | Rotation driving motor | 4 | Catheter or guidewire clamp transmission component |
| 5 | Wheel driving motor | 6 | Catheter or guidewire driving wheel |
| 7 | Catheter or guidewire idler wheel | 8 | Fourth driving seat |
| 9 | Rotation driving seat | 10 | Three-way valve |
| L | Length direction of plate | | |

DETAILED DESCRIPTION OF THE EMBODIMENTS

Hereafter, the specific embodiments of the present application will be illustrated in detail in combination with the accompanying drawings. It should be understood that, the specific embodiments described here are only used to illustrate and explain the present application, but are not intended to limit the present application.

It should be noted that, when there is no conflict, the embodiments and the features in the embodiments of the present application may be combined with each other.

In the present application, unless otherwise illustrated, the orientation words such as "upper, lower, top, and bottom" that are used are usually serve as the terms for describing a mutual position relationship between individual components in a direction as shown in the drawings or in a vertical, perpendicular, or gravity direction.

The present application is intended to solve the problems of operational convenience and integration of a catheter or guidewire delivery system. During the interventional treatment, it is required to deliver the catheter or guidewire to the patient's tissues to be intervened, and then inject drugs to the tissues through the catheter or guidewire to achieve a treatment effect. However, in the process of the existing catheter or guidewire delivery, position of the catheter or guidewire proximal end, serving as the fixing end, needs to be regulated so as to cooperate with the movement of the catheter or guidewire distal end, resulting in that the operations during the catheter or guidewire delivery process are cumbersome, and thereby easily rendering that the medical catheter or guidewire cannot accurately reproduce the operations of the medical personnel, and it is relatively difficult for structural integration. Therefore, how to improve the accuracy and convenience of the operations, and the structural integration becomes a problem to which an attention is paid. The specific structure and function of the catheter or guidewire delivery system will be set forth in detail below.

Referring to FIGS. 1 to 7, the present application discloses a transluminal intervention system, which comprises multiple medical catheters or guidewires and a medical catheter or guidewire driver for driving the multiple medical catheters or guidewires. The medical catheter or guidewire driver comprises a base 110 and a regulation and control mechanism.

Specifically, the base 110 is configured to mount the medical catheters or guidewires, wherein the medical catheters or guidewires may comprise a guide wire, a catheter, a micro-guide wire, a micro-catheter, a full-exchange balloon catheter, or a fast-exchange balloon catheter, etc. By means of the base 110, the medical catheters or guidewires are integrated onto the base 110, thereby achieving structural compactness and a high integration level.

The regulation and control mechanism is fixedly mounted on the base 110 and comprises a first regulation and control assembly 200 and a second regulation and control assembly 300 arranged at intervals for driving the medical catheters or guidewires to rotate and move, wherein, the first regulation and control assembly 200 and the second regulation and control assembly 300 may be configured to drive different medical catheters or guidewires, and enable the corresponding medical catheters or guidewires rotatable, so as to regulate the deflection angle. In this way, the medical catheters or guidewires may run in a spiral manner under superposition of rotation and movement acting forces, so as to accurately reproduce the actions of the medical personnel, and thus, the different medical catheters or guidewires are allowed to cooperate with each other and move to the lesion site to treat the lesion, thereby completing the interventional treatment.

The first regulation and control assembly 200 comprises a first driving seat 210 and a second driving seat 220 for driving movement of the medical catheter or guidewire, as well as a first catheter or guidewire fixture 230 for fixing the medical catheter or guidewire and driving rotation of medical catheter or guidewire. The second control component 300 comprises a second catheter or guidewire fixture 310 for fixing the medical catheter or guidewire and driving rotation of the medical catheter or guidewire, and a third driving seat 320 for driving movement of the medical catheter or guidewire. By means of the first driving seat 210, the second driving seat 220, and the first catheter or guidewire fixture 230 which are fixed in positions, position of at least one medical catheter or guidewire may be regulated; and by means of the second catheter or guidewire fixture 310 and the third driving seat 320 which are fixed in position, position of one medical catheter or guidewire may be regulated, such that different medical catheters or guidewires may cooperate with each other without mutual interference, thereby achieving structural simplification and convenient operation. Further, within the first regulation and control assembly 200 and the second regulation and control assembly 300, the medical catheters or guidewires are configured to be curved. It may be understood that, the first regulation and control assembly 200 and the second control component 300 are fixed in positions, and by means of the two, different medical catheters or guidewires may be arranged to be curved. In this way, when a distal end of a corresponding medical catheter or guidewire is moved, the position of a proximal end of the medical catheter or guidewire does not need to be regulated adaptively, and the movement path of the medical catheter or guidewire may be limited, such that the medical catheter or guidewire may be orderly moved, thereby ensuring that a surgery is smoothly performed.

It should be noted that, the transluminal intervention system may be used in a full-exchange system or a fast-exchange system. Each system may comprise a corresponding medical catheter or medical wire, which is known to those skilled in the art and redundant descriptions thereof will be omitted for conciseness. The medical catheter and medical wire may comprise two ends, namely a proximal end of the medical catheter or guidewire and a distal end of the medical catheter or guidewire. The proximal end of the medical catheter or guidewire may be defined as one end that is located on the base 110, and the distal end of the medical catheter or guidewire may be defined as one end that can go deep into the human body.

Optionally, the base 110 may be in various shapes; and it may be a rectangular plate that is convenient for processing, or an L-shaped plate that is easy to grip, or may be in other irregular shapes. The base 110 may have a plate-like structure, a box-like structure, or a chassis-like structure that can satisfy the requirements of mounting the regulation and control mechanism, as long as it can be used for mounting the guide structure set and the delivery assemblies. A chassis-like structure is taken as an example. The chassis-like structure may be a sheet-like structure with a hollow-out portion, and the regulation and control mechanism may be embedded and mounted within the hollow-out portion, such that each regulation and control mechanism may be integrated on the base 110, thereby achieving structural compactness and effectively reducing external interference.

Optionally, with regard to the regulation and control mechanism, the structures of the first driving seat 210, the second driving seat 220, and the third driving seat 320 may be the same or different, and they are required to be able to drive movement of the corresponding medical catheters or guidewires. The driving seats may each comprise a driving element that is fixedly mounted on the base 110 and can provide a driving force, and a contact element that contacts with the medical catheter or guidewire and can output the driving force of the driving element. The contact component can generate a friction force with the medical catheter or guidewire to drive the medical catheter or guidewire it to move. In addition, the three driving seats may be located on a same side of the base 110 or mounted on different sides of the base 110, such that they may be flexibly mounted as required, thereby improving mounting efficiency.

Optionally, the structures of the first catheter or guidewire fixture 230 and the second catheter or guidewire fixture 310 may be the same or different, and they are required to be able to drive rotation of corresponding medical catheters or guidewires. The first catheter or guidewire fixture 230 is taken as an example, and it may comprise a driving element that is mounted on the base 110, and a fixing element that is mounted on the driving element and can fix the medical catheter or guidewire. In this way, when the driving element rotates, the medical catheter or guidewire is driven to rotate via the fixing element, that is, the corresponding medical catheter or guidewire is driven to self-rotate, such that the deflexion direction of the distal end of the medical catheter or guidewire is regulated. Of course, the first catheter or guidewire fixture 230 is not limited thereto, as long as it can clamp and fix the medical catheter or guidewire and drive it to rotate.

Figure 2:
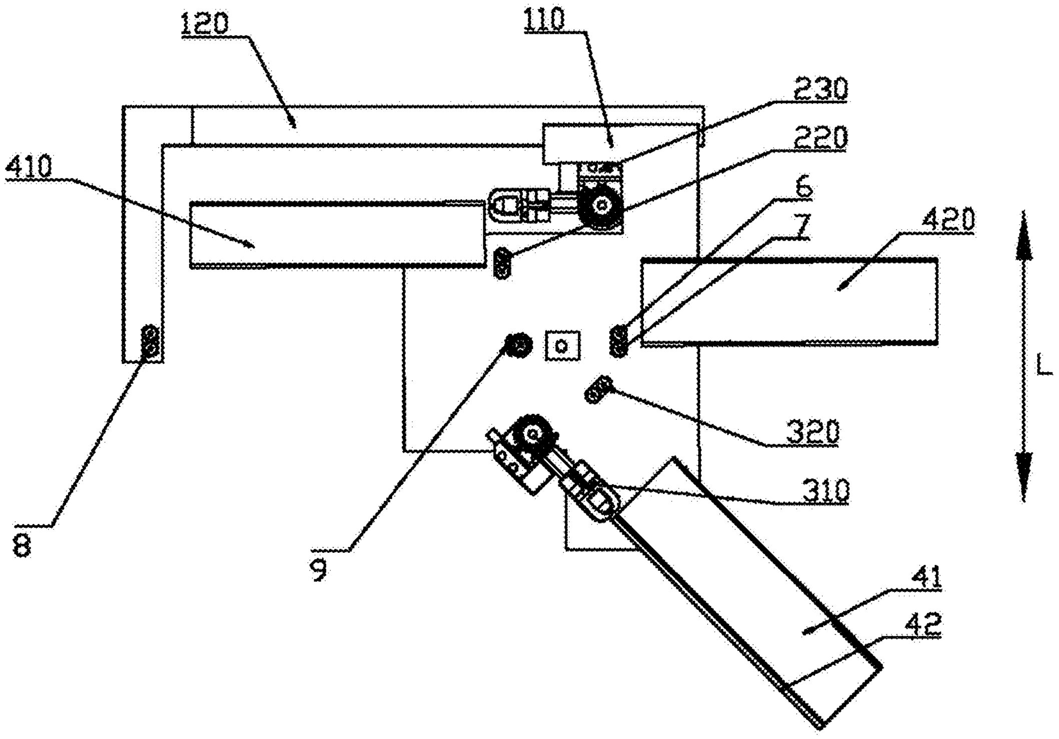
FIG. 2 is a schematic view of the structure of FIG. 1 at a different viewing perspective.

For the specific structure of the transluminal intervention system, in some embodiments, the base 110 comprises a base plate, and the regulation and control mechanism is inserted and fixed on the base plate, such that all of the multiple medical catheters or guidewires are arranged on the same side of the base plate at intervals, as shown in FIGS. 1 and 2. It may be understood that, the base 110 has a plate-like structure and may be configured to mount the regulation and control mechanism via the base plate, and the regulation and control mechanism can be inserted and mounted, thereby not only ensuring firm mounting of the regulation and control mechanism, but also achieving structural compactness and high integration level.

Further, the base plate may comprise a first base surface and a second base surface arranged oppositely, as well as a base peripheral wall surface surrounding the base plate and defining the shape of the base plate. The multiple medical catheters or guidewires may be mounted on either of the first base surface or the second base surface, thereby facilitating the mutual cooperation and switching of the multiple medical catheters or guidewires, while further improving the integration level of the transluminal intervention system. In addition, all of the multiple medical catheters are spaced apart from each other, thereby ensuring independent manipulation of each medical catheter or guidewire, preventing mutual interference, and ensuring that the system can accurately reproduce the surgical steps of the medical personnel.

Specifically, with regard to the position of the regulation and control mechanism, a case in which the regulation and control mechanism is mounted on the first base surface will be described as an example. The first base surface may be rectangular. In an embodiment, the first catheter or guidewire fixture 230, the second driving seat 220, the first driving seat 210, the third driving seat 320, and the second catheter or guidewire fixture 310 are sequentially arranged along a length direction L of the base plate at intervals. As shown in FIGS. 1 and 2, it may be understood that, if there is no mutual interference between individual regulation and control components, they may be arranged along the length direction L of the plate at intervals, such an arrangement not only can facilitate mounting operations, but also can fully utilize the structure of the base plate for mounting, thereby achieving structural compactness and improving system integration level.

Further, two or three or more medical catheters or guidewires may be included in the system, wherein the first catheter or guidewire fixture 230 and the second driving seat 220 may be a combination unit and are configured to drive the same medical catheter or guidewire, the first driving seat 210 may be configured to drive another medical catheter or guidewire, and the third driving seat 320 and the second catheter or guidewire fixture 310 may be arranged as another combination unit to drive another same medical catheter or guidewire. In a case that the first catheter or guidewire fixture 230 and the second driving seat 220 are taken as examples, a catheter or guidewire proximal end of the medical catheter or guidewire may be fixed on the first catheter or guidewire fixture 230 to enable the catheter or guidewire proximal end to rotate, and a catheter or guidewire distal end of the medical catheter or guidewire may pass through the second driving seat 220, at this time, the catheter section of the medical catheter or guidewire may be clamped on the second driving seat 220 to enable the medical catheter or guidewire to linearly move. In this way, the rotation of the catheter or guidewire proximal end may be transmitted to the catheter or guidewire distal end to enable the catheter or guidewire distal end to be subjected to angle deviation, such that, in superposition with the linear movement of the catheter or guidewire distal end, a spiral running manner is enabled, so as to accurately reproduce the actions of the medical personnel, thereby efficiently and accurately completing a surgical treatment.

In some embodiments, the base plate is provided thereon with multiple guide structures 400 for regulating deflection of the medical catheters or guidewires, and the multiple guide structures 400 are arranged along the length direction L of the base plate at intervals. The corresponding medical catheters or guidewires may be limited in position by the guide structures 400, and the multiple guide structures 400 are arranged at intervals, such that the individual medical catheters or guidewires will not interfere with each other and run smoothly. More importantly, the guide structures may enable the medical catheters or guidewires to deflect, such that the medical catheters or guidewires may be arranged to be curved, so as to limit the movement paths of the medical catheters or guidewires, to allow the medical catheters or guidewires to orderly move, thereby ensuring that a surgery is smoothly performed.

Figure 3:
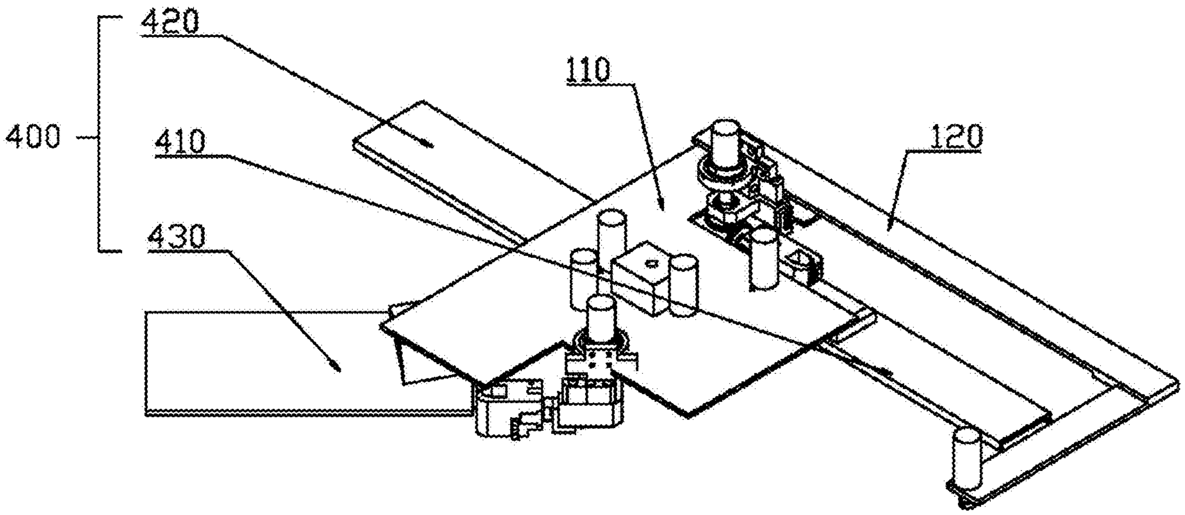
FIG. 3 is a schematic view of the stereostructure of FIG. 1 at a different viewing perspective, in which guide structures, a base, and fixing seats are shown.

Further, in an embodiment, the guide structure 400 comprises a first guide structure 410 for regulating the medical catheter or guidewire between the first catheter or guidewire fixture 230 and the second driving seat 220, a second guide structure 420 for regulating the medical catheter or guidewire between the second driving seat 220 and the first driving seat 210, and a third guide structure 430 for regulating the medical catheter or guidewire between the third driving seat 320 and the second catheter or guidewire fixture 310. As shown in FIGS. 1 and 3, it may be understood that, one medical catheter or guidewire may be provided between the first catheter or guidewire fixture 230 and the second driving seat 220, and the first guide structure 410 may be located on one side of the first catheter or guidewire fixture 230 and the second driving seat 220, and is provided with an opening facing the first catheter or guidewire fixture 230 and the second driving seat 220. The medical catheter or guidewire that extends from the first catheter or guidewire fixture 230 can protrude out of the second driving seat 220, after being deflected along the first guide structure 410. Therefore, by means of the first guide structure 410, the curvature and orderliness of the medical catheter or guidewire is ensured.

Furthermore, in an embodiment, the first guide structure 410, the second guide structure 420, and the third guide structure 430 are same in structure and each comprise: a bottom plate 41, fixedly mounted on the base plate; and two limit plates 42, configured to limit a movement range of the medical catheter or guidewire and arranged on the bottom plate 41 at intervals. As shown in FIGS. 1 and 2, it may be understood that, the bottom plate 41 comprises a top surface for supporting the medical catheter or guidewire, and the top surface of the bottom plate 41 is formed with a flat guide portion for coiling the medical catheter or guidewire. The top surface may be a flat surface, such that the medical catheter or guidewire may be always allowed to move smoothly, thereby ensuring order movement of the medical catheter or guidewire. The medical catheter or guidewire located on the guide structure 400 comprises two straight sections that fit the limit plates 42 and a natural arc-shaped section that is connected between the two straight sections. A spacing between the two straight sections may be regulated and limited by means of the limit plates 42.

Figure 6:
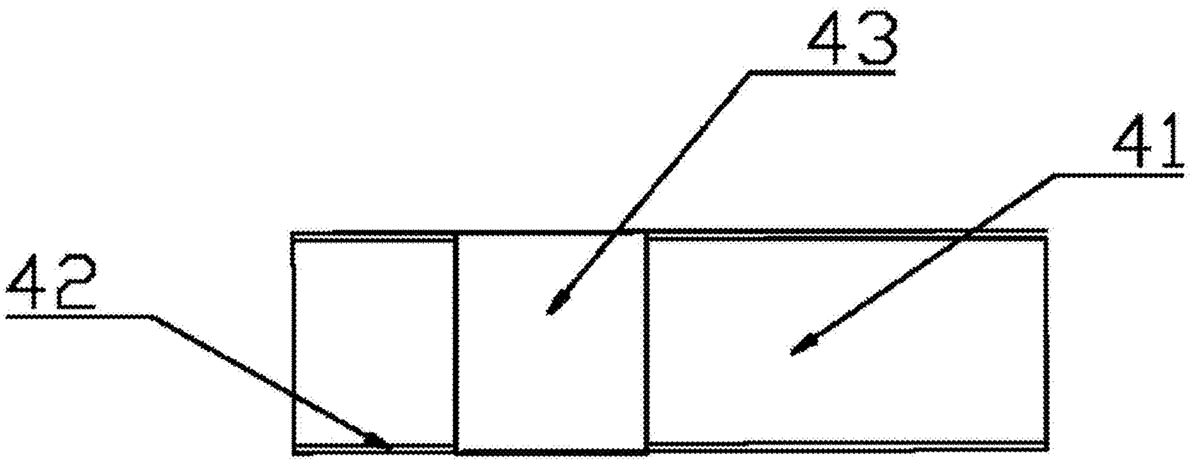
FIG. 6 is a schematic view of a guide structure in a transluminal intervention system according to a specific embodiment of the present application.

In some embodiments, a cover plate 43 is provided between the two limit plates 42, and a limiting accommodation space is formed between the cover plate 43 and the bottom plate 41, as shown in FIG. 6. At this time, in one or more of the first guide structure 410, the second guide structure 420, and the third guide structure 430, the cover plate 43 may be provided at the top of the two limit plates 42 to effectively prevent the medical catheter or guidewire falling off along a height direction of the limit plates 42, thereby ensuring the orderly running of the medical catheter or guidewire. The cover plate 43 may be an arc-shaped cover plate 43 that is projected upward, such that the limiting accommodation space is increased, thereby ensuring orderly running of medical catheter or guidewire; and it may also be a flat and straight plate, which is easy to process and has a low production cost.

Figure 4:
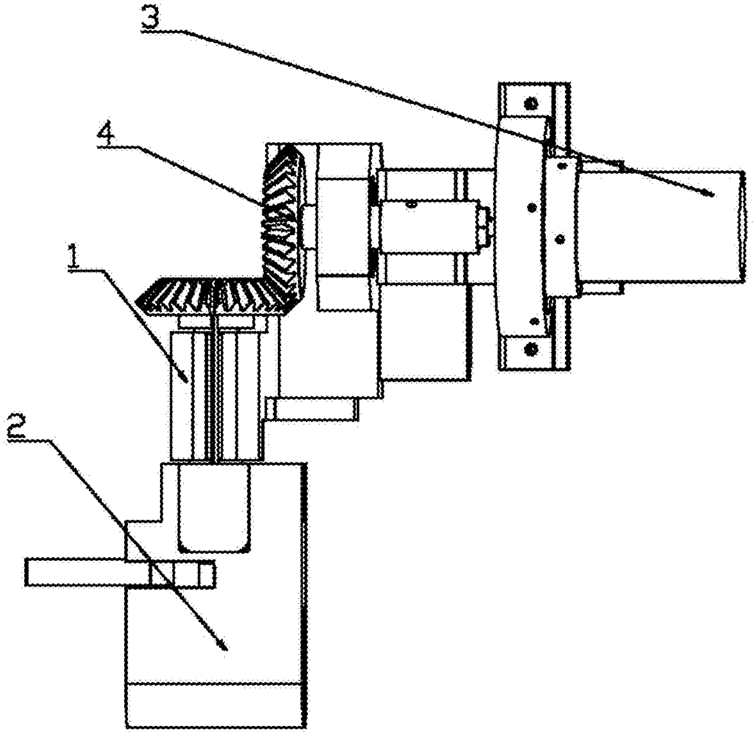
FIG. 4 is a schematic view of a local stereostructure of FIG. 1 at a different viewing perspective, in which a first catheter or guidewire fixture is shown.

In one aspect, in some embodiments, the first catheter or guidewire fixture 230 and the second catheter or guidewire fixture 310 are same in structure and each comprise a fixing seat bracket 1 protruding from the base plate and a catheter or guidewire clamp 2 rotatably mounted on the fixing seat bracket 1, as shown in FIGS. 3 and 4. It may be understood that, the base plate is formed thereon with a through hole, and the fixing seat bracket 1 may pass through the through hole, that is, one part of the fixing seat bracket 1 is located on one side of the base plate, and the other part thereof is located on the other side of the base plate. The fixing seat bracket 1 may be provided thereon with a mounting sleeve, and the catheter or guidewire clamp 2 may be provided with a shaft rod at one end thereof, which may pass through the mounting sleeve, such that the catheter or guidewire clamp 2 may be closer to the base plate, thereby improving the structural integration level.

Further, in some embodiments, the base plate is provided with a catheter or guidewire clamp driving unit for driving rotation of the catheter or guidewire clamp 2. The catheter or guidewire clamp driving unit comprises: a rotation driving motor 3 embedded on the base plate; and a catheter or guidewire clamp transmission component 4, connected between the rotation driving motor 3 and the catheter or guidewire clamp 2 in a transmission manner. As shown in FIGS. 3 and 4, by means of the rotation driving motor 3 which is embedded on the base plate, the structural integration level is improved. The catheter or guidewire clamp transmission component 4 may be a rotation shaft, the fixing seat bracket 1 may be provided thereon with another mounting sleeve, and the rotation shaft may be directly connected to the rotation driving motor 3 and output power to the shaft rod by passing through this mounting sleeve, thereby achieving order rotation of the catheter or guidewire clamp 2.

Furthermore, in an embodiment, the catheter or guidewire clamp transmission component 4 is a bevel gear transmission component and comprises a main drive gear protruding from the rotation driving motor 3 and a driven gear protruding from the catheter or guidewire clamp 2 which are meshed with each other. As shown in FIG. 4, the driven gear may be directly connected to the shaft rod, so as to allow the medical catheter or guidewire to rotate synchronously with the driven gear. The main drive gear is directly connected to the catheter or guidewire clamp transmission component 4, the driven gear is meshed with the main drive gear, and the rotation driving motor 3 sequentially drives the rotation shaft, the main drive gear, the driven gear, the shaft rod, and the catheter or guidewire clamp 2 to rotate, thereby achieving the driving of medical catheter or guidewire. The catheter or guidewire clamp 2 may be a guide wire fixing clamp that may be opened and closed, and the specific structure thereof is not limited here. In addition, the transmission component may also be a straight gear transmission component, an oblique gear transmission component, or a friction wheel transmission component.

Figure 5:
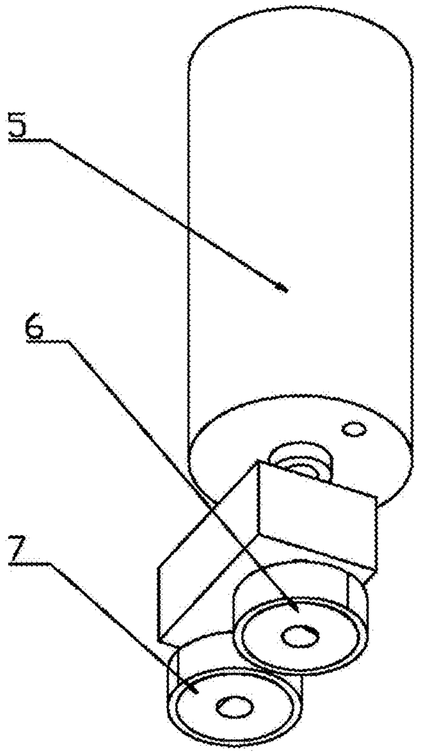
FIG. 5 is a schematic view of a local stereostructure of FIG. 1 at a different viewing perspective, in which first driving seat is shown.

In another aspect, in an embodiment, the first driving seat 210, the second driving seat 220, and the third driving seat 320 are same in structure and each comprises a wheel driving motor 5 that is mounted on the base plate, as well as a catheter or guidewire driving wheel 6 and a catheter or guidewire idler wheel 7 protruding from the base plate, as shown in FIGS. 2, 3, and 5. The wheel driving motor 5 may drive the catheter or guidewire driving wheel 6 to rotate, and since the medical catheter or guidewire is clamped between the catheter or guidewire driving wheel 6 and the catheter or guidewire idler wheel 7, there is frictional force formed between the catheter or guidewire driving wheel 6 and the medical catheter or guidewire, and when the catheter or guidewire driving wheel 6 rotates, its rotational force allows the medical catheter or guidewire to move linearly via the frictional force, thereby achieving accurate and quick driving of the medical catheter or guidewire.

Further, in an embodiment, both of an axis of the catheter or guidewire driving wheel 6 and an axis of the catheter or guidewire idler wheel 7 are perpendicular to the base plate, as shown in FIG. 1. In this way, the catheter or guidewire driving wheel 6 and the catheter or guidewire idler wheel 7 may be spaced from the base plate at a smaller interval, and a driving force in a direction parallel to the base plate may be generated on the medical catheter or guidewire, thereby achieving a more structural compactness and a high integration level. And/or, in another embodiment, the wheel driving motor 5 and the medical catheter or guidewire are arranged on two sides of the base plate, as shown in FIGS. 1 and 3. It may be understood that, all of multiple wheel driving motors 5 may be located on a second base surface, while all of the medical catheters or guidewires may be located on a first base surface, so as to not only improve the structural compactness, but also avoid interference of the wheel driving motors 5 on the medical catheters or guidewires, thereby ensuring stable running of the medical catheters or guidewires.

In some embodiments, a driving direction of the first driving seat 210 is opposite to a driving direction of the second driving seat 220. As shown in FIGS. 1 and 2, since the distal end of the medical catheter or guidewire protruding from the first catheter or guidewire fixture 230 needs to pass through the second driving seat 220 and the first driving seat 210, the opposite driving directions of the second driving seat 220 and the first driving seat 210 can ensure smooth movement of the medical catheter or guidewire. And/or, in an embodiment, a driving direction of the third driving seat 320 is the same as the driving direction of the first driving seat 210. As shown in FIG. 2, the first driving seat 210 and the third driving seat 320 are configured to drive different medical catheters or guidewires. With the consistency of their driving directions, the distal ends of different medical catheters or guidewires can move towards a direction of the patient's lesions, thereby ensuring the fastness and accuracy of surgical operations.

In an embodiment, the medical catheter or guidewire driver comprises a fixing seat 120, and the base 110 that is slidably mounted on the fixing seat 120 and can slide along a length direction of the fixing seat 120, as shown in FIG. 1. It may be understood that, a chassis body of the system consists of the fixing seat 120 and the base 110, wherein the position relationship between the fixing seat 120 and the patient may be relatively fixed, whereas the base 110 may slide along the fixing seat 120 so as to regulate the relative position of the base 110 and the patient, such that the base 110 may be adaptively regulated according to the length of the medical catheter entering the human body.

Specifically, in an embodiment, the regulation and control mechanism further comprises a third regulation and control assembly for driving rotation and movement of the medical catheter or guidewire. The third regulation and control assembly comprises: a fourth driving seat 8, configured to drive movement of the medical catheter or guidewire and fixedly mounted on the fixing seat 120; and a rotation driving seat 9, fixedly mounted on the base plate and configured to fix and drive rotation of the medical catheter or guidewire, as shown in FIGS. 2 and 3. It may be understood that, the medical catheter or guidewire may comprise a catheter, wherein the catheter has a relatively large diameter and can allow entrance of a guide wire or a balloon catheter etc. for entry, and thus, the bendability of the catheter is relatively poor as compared to the guide wire. The catheter may include a catheter proximal end and a catheter distal end, wherein, the catheter proximal end may be mounted on the rotation driving seat 9, and the catheter distal end may pass through the fourth driving seat 8. The deflection angle of the catheter distal end may be regulated by the rotation driving seat 9, and the catheter distal end may be driven by the fourth driving seat 8 to move linearly. In this way, under the superposition of rotation and linear movement, the doctor's operating actions may be accurately reproduced, thereby ensuring that a surgery is smoothly performed. It should be noted that the fourth driving seat 8 may have a same structure as with the first driving seat 210, and redundant descriptions thereof is omitted herein.

Further, in an embodiment, the fixing seat 120 comprises an L-shaped plate, which comprises a first directional plate portion and a second directional plate portion that are sequentially connected, the base plate is provided with a sliding component on a surface thereof, and the first directional plate portion is provided with a sliding rail for sliding the sliding component on a surface thereof. By means of the slide rail and the sliding component, regulation of a spacing between the second base plate and the base 110 is achieved. It may be understood that, the fourth driving seat 8 may be located on the second directional plate portion, such that, when the catheter distal end moves linearly, in order to avoid dragging the catheter, the spacing between the second directional plate portion and the base 110 may be adaptively regulated, thereby ensuring the safety and effectiveness of the catheter.

Figure 7:
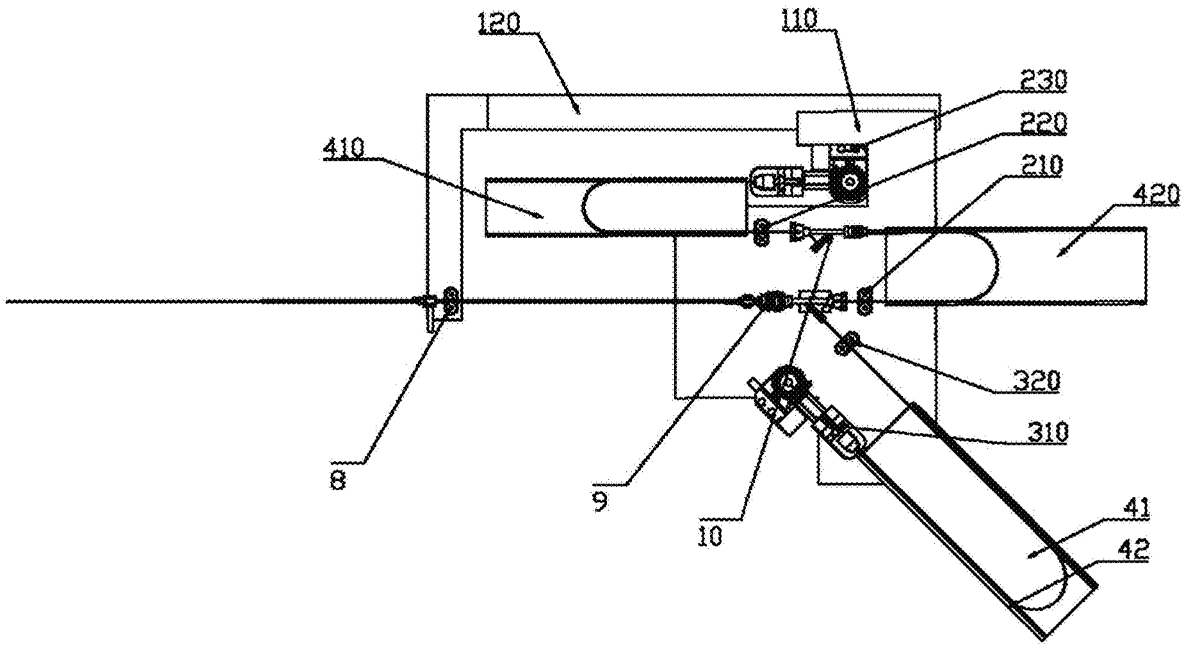
FIG. 7 is a schematic view of a transluminal intervention system according to a specific embodiment of the present application in a used state.

In the following, a method of using the transluminal intervention system will be exemplified. Specifically, as shown in FIG. 7, a medical catheter or guidewire may comprise a catheter that is mounted on the fourth driving seat 8 and the rotation driving seat 9; a guide wire that is sequentially mounted on the second catheter fixture 310 and the third driving seat 320 and can go deep into the catheter; a micro-guide wire that is sequentially mounted on the first catheter fixture 230, the second driving seat 220 and the first driving seat 210 and can go deep into the catheter; and a micro-catheter that is sleeved on the micro-guide wire. A three-way valve 10 may be provided on the base 110 between the second driving seat 220 and the second guide structure 420. A proximal end of the micro-catheter may be mounted on the three-way valve 10, and a distal end of the micro-catheter may be clamped on the first driving seat 210. The micro-guide wire is inserted into the micro-catheter along the three-way valve 10 and can pass through the micro-catheter. The specific steps are as follows: firstly, a guide wire distal end of the guide wire can pass through the catheter and is moved to a first designated position, for example, to a position of a large blood vessel of the tissues to be treated; secondly, a catheter distal end of the catheter is moved along the guide wire to the first designated position and the guide wire is pulled out; thirdly, a distal end of the micro-wire is moved to a second designated position, for example, to a position of a small blood vessel of the tissues to be treated; and finally, the micro-catheter is moved along the micro-wire to the second designated position, and a drug is injected into the micro-catheter through the three-way valve 10, so as to perform drug treatment to the tissues to be treated through the micro-catheter, thereby completing a interventional surgical treatment.

Further, the micro-guide wire is taken as an example, and the more specific steps are as follows: a proximal end of the micro-guide wire may be fixed on the first catheter or guidewire fixture 230, and the distal end of the micro-guide wire can pass through the second driving seat 220 and the first driving seat 210 after passing around the first guide structure 410. When the first catheter or guidewire fixture 230 is started, the curvedly-arranged micro-guide wire can be rotated, and a rotating force is transmitted to the distal end of the micro-guide wire to allow it to deflect at a certain angle, and at the same time, a driving force for linear movement may be provided to the micro-guide wire by the second driving seat 220 and the force is transmitted to the distal end of the micro-guide wire to drive the distal end of the micro-guide wire to move linearly, such that, a rotation driving force and a linear movement force are superposed to the distal end of the medical catheter or guidewire, thereby enabling the micro-guide wire to run in a spiral manner, accurately reproducing the operations of the medical personnel and ensuring that an intervention surgery is stably performed. In addition, a U-shaped motion locus of the micro-guide wire can be formed on the first guide structure 410, such that, the movement of the micro-guide wire may be achieved without regulating a spacing between the first catheter or guidewire fixture 230 and the second driving seat 220, thereby improving delivery efficiency of the micro-guide wire. The micro-guide wire has a regular running and is convenient to operate, avoiding folding of the micro-guide wire during the delivery process and ensuring channel smoothness of the micro-guide wire.

It should be noted that, the other components and functions of the transluminal intervention system according to the embodiments of the present application are known to those skilled in the art, and redundant descriptions thereof are omitted for conciseness.

The preferred embodiments of the present application are described in detail above in combination with the accompanying drawings. However, the present application is not limited to the specific details of the above embodiments, and various simple modifications (such as changes in the shape, thickness, and material of an end plate sealing layer) may be made to the technical solutions of the present application within the scope of the technical concept of the present application, all of which fall within the protection scope of the present application.

In addition, it should be noted that, in the description of the present specification, the description with reference to terms such as "one embodiment", "some embodiments", "example", "specific example", or "some examples" etc. means that the specific features, structures, materials, or features described in combination with the embodiment or example are contained in at least one embodiment or example of the present application. In the present specification, the schematic expressions of the above terms are not necessarily directed at the same embodiment or example. Moreover, the specific features, structures, materials, or features that are described may be combined in any one or more of the embodiments or examples in an appropriate manner. If there is no contradiction, they may be combined in any appropriate manner. In order to avoid unnecessary repetitions, various possible combinations will not be otherwise illustrated in the present application.

In addition, various different embodiments of the present application may also be combined arbitrarily, as long as the combinations will not depart from the idea of the present application, and they should also be regarded as the content disclosed in the present application.

The invention claimed is:

1. A transluminal intervention system; comprising:
multiple medical catheters or guidewires; and
a medical catheter or guidewire driver for driving the multiple medical catheters or guidewires, wherein; the medical catheter or guidewire driver comprises:
a base; and
a regulation and control mechanism, fixedly mounted on the base and comprising:
a first regulation and control assembly; and
a second regulation and control assembly, wherein the first and second regulation and control assemblies are arranged at intervals and for driving the multiple medical catheters or guidewires to rotate and move; and
wherein the first regulation and control assembly comprises:
a first driving seat and a second driving seat for driving movement of the medical catheters or guidewires; and
a first catheter or guidewire fixture for fixing the medical catheters or guidewires and driving rotation of the medical catheters or guidewires; and
wherein the second regulation and control assembly comprises:
a second catheter or guidewire fixture for fixing the medical catheters or guidewires and driving rotation of the medical catheters or guidewires; and
a third driving seat for driving movement of the medical catheters or guidewires; and
wherein the multiple medical catheters or guidewires are curved within the first regulation and control assembly and within the second regulation and control assembly.

2. The transluminal intervention system of claim 1, wherein:
the base comprises a base plate;
the regulation and control mechanism is inserted and fixed on the base plate; and
the multiple medical catheters or guidewires are arranged on a same side of the base plate at intervals.

3. The transluminal intervention system of claim 2, wherein the medical catheter or guidewire driver comprises:
a fixing seat; and
the base that is slidably mounted on the fixing seat and able to slide along a length direction of the fixing seat.

4. The transluminal intervention system of claim 3, wherein the regulation and control mechanism further comprise a third regulation and control assembly for driving rotation and movement of the medical catheters or guidewires, and wherein the third regulation and control assembly comprises:
a fourth driving seat, configured to drive movement of the medical catheters or guidewires and fixedly mounted on the fixing seat; and
a rotation driving seat, fixedly mounted on the base plate and configured to fix the medical catheters or guidewires and drive rotation of the medical catheters or guidewires.

5. The transluminal intervention system of claim 4, wherein;
the fixing seat comprises an L-shaped plate;
the L-shaped plate comprises a first directional plate portion and a second directional plate portion that are sequentially connected;
a sliding component is provided on a surface of the base plate; and
the first directional plate portion is provided with a sliding rail for sliding the sliding component.

6. The transluminal intervention system of claim 2, wherein; the first catheter or guidewire fixture, the second driving seat, the first driving seat, the third driving seat, and the second catheter or guidewire fixture are sequentially arranged along a length direction of the base plate at intervals.

7. The transluminal intervention system of claim 6, wherein, the base plate is provided with multiple guide structures for regulating deflection of the medical catheters or guidewires, and the multiple guide structures are arranged along the length direction of the base plate at intervals.

8. The transluminal intervention system of claim 7, wherein; the multiple guide structures comprise;
a first guide structure for regulating the medical catheters or guidewires between the first catheter or guidewire fixture and the second driving seat;

a second guide structure for regulating the medical catheters or guidewires between the second driving seat and the first driving seat; and a third guide structure for regulating the medical catheters or guidewires between the third driving seat and the second catheter or guidewire fixture.

9. The transluminal intervention system of claim 8, wherein, the first guide structure, the second guide structure, and the third guide structure are same in structure and each comprises:

a bottom plate, fixedly mounted on the base plate; and two limit plates, configured to limit a movement range of the medical catheters or guidewires and arranged on the bottom plate at intervals.

10. The transluminal intervention system of claim 9, wherein, a cover plate is provided between the two limit plates, and wherein a limiting accommodation space is formed between the cover plate and the bottom plate.

11. The transluminal intervention system of claim 6, wherein; the first catheter or guidewire fixture and the second catheter or guidewire fixture are same in structure, and wherein each of the first and the second catheter or guidewire fixtures comprises a fixing seat bracket, protruding from the base plate, and a catheter wire clamp rotatably mounted on the fixing seat bracket.

12. The transluminal intervention system of claim 11, wherein, the base plate is provided with a catheter or guidewire clamp driving unit for driving rotation of the catheter or guidewire clamp, and wherein the catheter or guidewire clamp driving unit comprises:

a rotation driving motor, embedded on the base plate; and a catheter or guidewire clamp transmission component, connected between the rotation driving motor and the catheter or guidewire clamp in a transmission manner.

13. The transluminal intervention system of claim 12, wherein, the catheter or guidewire clamp transmission component is a bevel gear transmission component comprising:

a main drive gear protruding from the rotation driving motor; and a driven gear protruding from the catheter or guidewire clamp and meshed with the main drive gear.

14. The transluminal intervention system of claim 6, wherein; the first driving seat, the second driving seat, and the third driving seat are same in structure and each comprising:

a wheel driving motor mounted on the base plate;

a catheter or guidewire driving wheel protruding from the base plate; and a catheter or guidewire idler wheel protruding from the base plate, wherein the medical catheters or guidewires are clamped between the catheter or guidewire driving wheel and the catheter or guidewire idler wheel.

15. The transluminal intervention system of claim 14, wherein;

both of an axis of the catheter or guidewire driving wheel and an axis of the catheter or guidewire idler wheel are perpendicular to the base plate; or the wheel driving motor and the medical catheters or guidewires are arranged on two sides of the base plate, respectively.

16. The transluminal intervention system of claim 6, wherein:

a driving direction of the first driving seat is opposite to a driving direction of the second driving seat; or a driving direction of the third driving seat is the same as the driving direction of the first driving seat.

* * * * *